(12) United States Patent
Krusell et al.

(10) Patent No.: US 6,325,706 B1
(45) Date of Patent: *Dec. 4, 2001

(54) USE OF ZETA POTENTIAL DURING CHEMICAL MECHANICAL POLISHING FOR END POINT DETECTION

(75) Inventors: Wilbur C. Krusell, Palo Alto; Andrew J. Nagengast, Sunnyvale; Anil K. Pant, Santa Clara, all of CA (US)

(73) Assignee: Lam Research Corporation, Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/182,570

(22) Filed: Oct. 29, 1998

(51) Int. Cl.[7] .......................... B24B 21/00; B24B 21/02; B24B 29/00; B24B 5/00
(52) U.S. Cl. ........................... 451/296; 451/299; 451/307
(58) Field of Search .................................. 451/303, 307, 451/296, 299, 300

(56) References Cited

U.S. PATENT DOCUMENTS

| | | | |
|---|---|---|---|
| 4,793,895 | 12/1988 | Kaanta et al. | 156/627 |
| 5,078,801 | * 1/1992 | Malik | 134/29 |
| 5,240,552 | 8/1993 | Yu et al. | 156/636 |

(List continued on next page.)

FOREIGN PATENT DOCUMENTS

WO 85/04486   10/1985   (WO).

OTHER PUBLICATIONS

Chingfu Lin, Shie–Sen Peng, Hsin Chu, "Pad Temperature As An End Point Detection Method In WCMP Process," 1998 CMP MIC Conference, Feb. 19–20, 1998, pp. 52–56.
"Zeta Potential: A Complete Course in 5 Minutes," Zeta–Meter, Inc. brochure, pp. 1–8.
"Coulter Delsa 440 SX, Zeta Potential and Particle Size," Coulter International Corp., 1996–1988 pp. 1–3.
D.H. Everett, Basic Principles of Colloid Science, Chapter 6, "Some Important Properties of Colloids I Kinetic Properties," Royal Society of Chemistry Paperbacks, Thomas Graham House, Cambridge, CB4 4WF, pp. 76–79 and 88–91.
Denny A. Jones—2nd ed., Principles and Prevention of Corrosion, Chapter 2, "Thermodynamics and Electrode Potential," ISBN 0–13–359993–0, Prentice–Hall International, 1996.

(List continued on next page.)

Primary Examiner—Allen Ostrager
Assistant Examiner—William Hong
(74) Attorney, Agent, or Firm—Brinks Hofer Gilson & Lione (57) ABSTRACT

A technique for utilizing a sensor to monitor fluid pressure from a fluid bearing located under a polishing pad to detect a polishing end point. A sensor is located at the leading edge of a fluid bearing of a linear polisher, which is utilized to perform chemical-mechanical polishing on a semiconductor wafer. The sensor monitors the fluid pressure to detect a change in the fluid pressure during polishing, which change corresponds to a change in the shear force when the polishing transitions from one material layer to the next. In order to ensure that there is a noticeable difference in the shear force variation at the polishing end point, a slurry having a particular pH level is selected. The pH level ensures that the zeta potential changes noticeably from one material to the next, so as to induce a change in the shear force, which is detected by a change in the fluid pressure.

23 Claims, 10 Drawing Sheets

U.S. PATENT DOCUMENTS

| | | | |
|---|---|---|---|
| 5,265,378 | * 11/1993 | Rostoker | 51/165.75 |
| 5,272,117 | * 12/1993 | Roth et al. | 437/228 |
| 5,308,438 | 5/1994 | Cote et al. | 156/636 |
| 5,321,304 | 6/1994 | Rostoker | 257/621 |
| 5,329,732 | 7/1994 | Karlsrud et al. | 51/131.5 |
| 5,409,544 | 4/1995 | Ota et al. | 134/22.14 |
| 5,433,651 | 7/1995 | Lustig et al. | 451/6 |
| 5,527,423 | * 6/1996 | Neville et al. | 156/636.1 |
| 5,558,568 | * 9/1996 | Talieh et al. | 451/303 |
| 5,593,344 | * 1/1997 | Weldon et al. | 451/296 |
| 5,668,063 | 9/1997 | Fry et al. | 438/5 |
| 5,692,947 | 12/1997 | Talieh et al. | 451/41 |
| 5,722,877 | 3/1998 | Meyer et al. | 451/41 |
| 5,762,536 | * 6/1998 | Pant et al. | 451/6 |
| 5,800,248 | * 9/1998 | Pant et al. | 451/41 |
| 5,944,580 | 8/1999 | Kim et al. | 451/9 |
| 5,980,368 | 11/1999 | Chang et al. | 451/303 |
| 6,186,865 | * 2/2001 | Thornton et al. | 451/8 |

OTHER PUBLICATIONS

Diane Hymes, Igor Malik, Jackie Zhang, Ramin Emami, "Brush scrubbing emerges as future wafer–cleaning technology," Solid State Technology, 0038–111X, Jul. 1997, pp. 209–214.

Brad Withers, Eugene Zhao, Wilbur Krusell, Rahul Jairath, "Wide Margin CMP for STI," Solid State Technology, Jul. 1996, pp. 173–179.

D.R. Crow, 4th ed., Principles and Applications of Electrochemistry, ISBN 0 7514 0158 4 (PB), Blackie Academic and Professional, 1994, pp. 76–77.

R.J. Gutmann, D.T.Price, J.M. Neirynck, C. Sainio, D. Permana, D.J. Duquette and S.P. Murarka, "CMP of Copper–Polymer Interconnect Structures,"CMP–MIC Conference, 1998 IMIC–300P/98/0257, Feb. 19–20, 1998, pp. 257–266.

International Search Report For PCT/US99/23662.

* cited by examiner

USE OF ZETA POTENTIAL DURING CHEMICAL MECHANICAL POLISHING FOR END POINT DETECTION

RELATED APPLICATION

This application is related to co-pending application titled "Apparatus And Method For Performing End Point Detection On A Linear Planarization Tool;" Ser. No. 09/182,532; filed Oct. 29, 1998.

BACKGROUND OF THE INVENTION

1. Field of the Invention

The present invention relates to the field of semiconductor wafer processing and, more particularly, to performing end-point detection on a linear planarization tool used to planarize semiconductor wafers.

2. Background of the Related Art

The manufacture of an integrated circuit (IC) device requires the formation of various layers above a base semiconductor substrate, in order to form embedded structures over or in previous layers formed on the substrate. During the manufacturing process, certain portions of these layers need complete or partial removal to achieve the desired device structure. With diminishing feature size, such structures result in highly irregular surface topography causing manufacturing problems in the formation of thin film layers. To facilitate manufacturing processes, the rough surface topography has to be smoothened or planarized.

One of the methods for achieving planarization of the surface is chemical mechanical polishing (CMP). CMP is being extensively pursued to planarize a surface of a semiconductor wafer, such as a silicon wafer, at various stages of integrated circuit processing. CMP is also used in flattening optical surfaces, metrology samples, and various metal and semiconductor based substrates.

CMP is a technique in which a chemical slurry is used along with a polishing pad to polish away materials on a semiconductor wafer. The mechanical movement of the pad relative to the wafer, in combination with the chemical reaction of the slurry disposed between the wafer and the pad, provide the abrasive force with chemical erosion to planarize the exposed surface of the wafer (typically, a layer formed on the wafer), when subjected to a force pressing the wafer onto the pad. In the most common method of performing CMP, a substrate is mounted on a polishing head which rotates against a polishing pad placed on a rotating table (see, for example, U.S. Pat. No. 5,329,732). The mechanical force for polishing is derived from the rotating table speed and the downward force on the head. The chemical slurry is constantly transferred under the polishing head. Rotation of the polishing head helps in the slurry delivery, as well as in averaging the polishing rates across the substrate surface.

Another technique for performing CMP to obtain a more effective polishing rate is using the linear planarization technology. Instead of a rotating pad, a moving belt is used to linearly move the pad across the wafer surface. The wafer is still rotated for averaging out the local variations, but the planarization uniformity is improved over CMP tools using rotating pads, partly due to the elimination of unequal radial velocities. One such example of a linear polisher is described in U.S. Pat. No. 5,692,947.

Unlike the hardened table top of a rotating polisher, linear planarizing tools are capable of using linearly moving belts upon which the pad is disposed. The ability for the belt to flex can cause a change in the pad pressure being exerted on the wafer. When the pressure of the wafer-pad engagement can be controlled, it provides a mechanism for adjusting the planarization rate and/or the polishing profile across the surface of the wafer. Therefore, a fluid support (or platen) can be placed under the belt for use in adjusting the pad pressure being exerted on the wafer. An example of a fluid support is disclosed in U.S. Pat. No. 5,558,568.

When CMP is employed, it is generally advantageous to monitor the effects of the planarizing process to determine if the process is being performed according to desired specifications. A monitoring problem specific to CMP is the determination of the process end point. That is, the ability to monitor the material thickness being removed and to terminate the polishing when a certain end point condition is reached. A typical end point is the case when one material is removed to exposed an underlying material, which is different from the first material. An end point detection technique detects this point where the CMP process is to be stopped.

Various schemes have been devised to detect an end point during CMP. For example, one technique relies on conductivity measurements (see for example, U.S. Pat. Nos. 4,793,895 and 5,321,304). Another technique employs the monitoring of the electrical current to a motor which rotates the wafer (see for example, U.S. Pat. No. 5,308,438). Still another technique uses an acoustic wave reflection to monitor dielectric thickness (see for example, U.S. Pat. No. 5,240,552). Optical techniques are now being implemented as an accurate indicator for measuring material thickness on a wafer (see for example, U.S. Pat. No. 5,433,651). Additionally, Chingfu Lin et al. have demonstrated the use of pad temperature as a method for the determination of polish end point (see, "Pad Temperature As An End Point Detection Method in WCMP Process;" 1998 CMP-MIC Conference; Feb. 19–20, 1998; pp. 52–56). Accordingly, it is understood that a number of techniques are available for detecting the end point of a polishing cycle for a semiconductor wafer.

The historical approaches for in-situ monitoring of the end point pertains mainly to rotating (orbital) polishers. Linear polishing techniques allow for alternative techniques to be developed to take advantage of the linearly moving pad/belt of the linear planarization tools. The present invention implements an end point detection scheme for CMP, which relies on an operative phenomenon different from previous techniques, but is still simple in its approach. The present invention is operative with linear planarization tools, but can be readily adapted to other techniques, including rotating polishers.

SUMMARY OF THE INVENTION

The present invention describes a technique for monitoring fluid pressure from a fluid bearing located under a polishing pad to detect a polishing end point. In the specific embodiment, a linear polisher, which employs a fluid bearing, is utilized to perform chemical-mechanical polishing on a semiconductor wafer. At least one sensor is distributed along the surface or coupled to an opening along the surface to determine the pressure of the fluid residing between the surface of the fluid bearing and the underside of the belt/pad assembly.

A leading edge pressure sensor is used to detect a change in the fluid pressure during polishing. When one material is polished away to expose a second material, the shear force being exerted at the wafer-pad interface changes, causing a corresponding change in the fluid pressure being sensed by the pressure sensor.

In order to ensure that there is a noticeable difference in the shear force variation at the polishing end point, the zeta potential property of the materials is exploited. In practicing the invention, a particular pH level for the slurry is selected, which pH level ensures that the zeta potential is appreciably different for the two materials involved. In the preferred technique the pH level selected ensures that there is a zeta potential polarity change when one material is polished away and the second material is exposed. The zeta potential polarity change ensures that a change in the shear force at the wafer-pad interface can be detected at the leading edge as a change in the fluid pressure.

DETAILED DESCRIPTION OF THE PREFERRED EMBODIMENTS

A scheme for detecting an end point during chemical mechanical polishing (CMP) when planarizing a wafer surface is described. In the following description, numerous specific details are set forth, such as specific structures, materials, slurries, tools, polishing techniques, etc., in order to provide a thorough understanding of the present invention. However, it will be appreciated by one skilled in the art that the present invention may be practiced without these specific details. In other instances, well known techniques, structures and processes have not been described in detail in order not to obscure the present invention. Furthermore, although the present invention is described in reference to performing CMP on a layer formed on a semiconductor wafer, the invention can be readily adapted to polish other materials as well, such as glass, metal substrates or other semiconductor substrates, including substrates for use in manufacturing flat panel displays.

Figure 1:
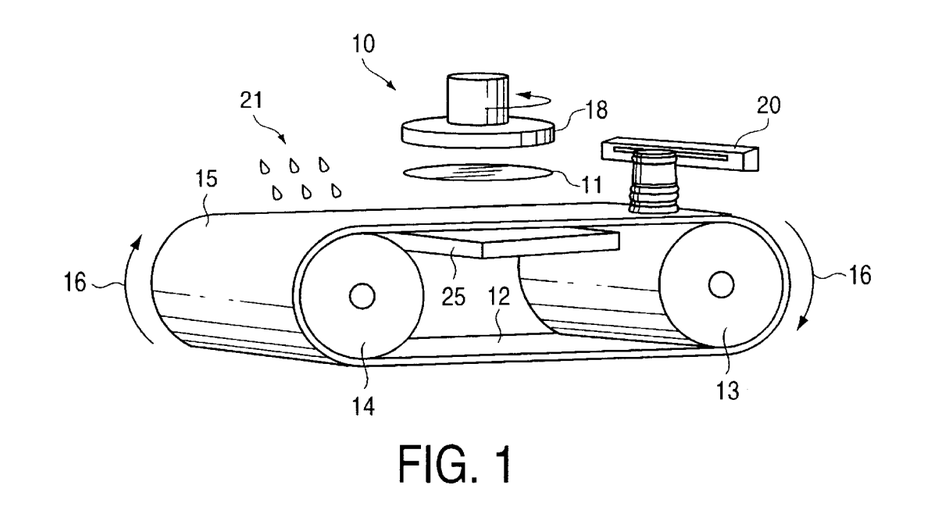
FIG. 1 is a pictorial illustration of a linear polisher which incorporates the present invention.

Referring to FIG. 1, a linear polisher 10 for use in practicing the present invention is shown. The linear polisher (also referred to as a linear planarization tool) 10 is utilized in planarizing a semiconductor wafer 11, such as a silicon wafer. Although CMP can be utilized to polish a base substrate, typically CMP is utilized to remove a material layer (such as a film layer) or a portion of the material layer deposited on the semiconductor wafer. Thus, the material being removed can be the substrate material of the wafer itself or one of the layers formed on the substrate. Formed layers include dielectric materials (such as silicon dioxide), metals (such as aluminum, copper or tungsten) and alloys, or semiconductor materials (such as silicon or polysilicon).

More specifically for IC fabrication, CMP is employed to planarize one or more of these layers fabricated on the wafer or is employed to expose an underlying topography while planarizing the surface. In many instances, CMP involves patterned features formed on the surface of a wafer. For example, a dielectric layer (such as silicon dioxide) may be deposited over the surface, covering both raised features, as well as the underlying dielectric layer. Then, CMP is used to planarize the overlying silicon dioxide, so that the surface is substantially planarized. It is desirable to stop the polishing process at a point the raised features are exposed.

In another technique, dual damascene structures are fabricated by the use of CMP. For example, via and contact trench openings are patterned and formed in an inter-level dielectric (ILD) layer residing on a semiconductor wafer. Subsequently, a metal, such as copper or aluminum, is deposited to fill in the via and trench openings. In the case of copper, a barrier layer (such as TiN, Ta, TaN, etc) is deposited into the openings first to operate as a barrier liner between the Cu and the ILD. Then, CMP is used to polish away the excess metal material residing over the ILD, so that the metal resides only in the via and trench openings. CMP allows for the surface of the contact region (upper portion of the dual opening) to have a substantially planar surface, while the metal above the surface of the ILD is removed. The formation and fabrication of dual damascene structures are known in the art.

Thus, CMP is utilized extensively to planarize film layers or formed features in which the planarization process is terminated at a particular point. In the dual damascene structure described above, the CMP is terminated when the metal is removed to expose the ILD. CMP ensures that the resultant structure has metal remaining only in the openings and that the upper surface of the ILD and the trench fill have a substantially planar surface. Generally, the art of performing CMP to polish away all or a portion of a layer formed on a wafer is known in the art.

The linear polisher 10 of FIG. 1 employs a linear planarization technology described above. The linear polisher 10 utilizes a belt 12, which moves linearly with respect to the surface of the wafer 11. The belt 12 is a continuous belt rotating about rollers (or spindles) 13 and 14, in which one roller or both is/are driven by a driving means, such as a motor, so that the rotational motion of the rollers 13, 14 causes the belt 12 to be driven in a linear motion (as shown by arrow 16) with respect to the wafer 11. The belt 12 is typically made from a metallic material. A polishing pad 15 is affixed onto the belt 12 at its outer surface facing the wafer 11. The pad can be made from a variety of materials, but is generally fibrous to provide an abrasive property. The belt can also be made from materials other than metal. In some instances, the pad 15 and the belt 12 are integrated as a single unit when fabricated. However constructed, the belt/pad assembly is made to move in a linear direction to planarize the wafer 11.

The wafer 11 typically resides within a wafer carrier 18, which is part of a polishing head. The wafer 11 is held in position by a mechanical retaining means, such as a retainer ring, and/or by the use of vacuum. Generally, the wafer 11 is rotated, while the belt/pad assembly moves in a linear direction 16 to polish a layer on the wafer 11. A downforce is exerted to press the polishing head and carrier 18 downward, in order to engage the wafer onto the pad with some predetermined force. The linear polisher 10 also dispenses a slurry 21 onto the pad 15. A variety of dispensing devices and techniques are known in the art for dispensing the slurry 21. A pad conditioner 20 is typically used in order to recondition the pad surface during use. Techniques for reconditioning the pad 15 are also known in the art and generally require a constant scratching of the pad in order to remove the residue build-up caused by the used slurry and removed waste material.

A support, platen or bearing 25 is disposed on the underside of belt 12 and opposite from the wafer 11, such that the belt/pad assembly resides between the bearing 25 and wafer 11. A primary purpose of bearing 25 is to provide a supporting platform on the underside of the belt 12 to ensure that the pad 15 makes sufficient contact with wafer 11 for uniform polishing. Since the belt 12 will depress when the wafer is pressed downward onto the pad 15, bearing 25 provides a necessary counteracting support to this downward force.

The bearing 25 can be a solid platform or it can be a fluid bearing (also referred to as a fluid platen or support). In the practice of the present invention, the preference is to have a fluid bearing, so that the fluid flow (shown by arrows 26 in FIG. 2) from the bearing 25 can be used to control forces exerted onto the underside of the belt 12. The fluid is generally air or liquid, although a neutral gas (such as nitrogen) can be used. By such fluid flow control, pressure variations exerted by the pad on the wafer can be adjusted to provide a more uniform polishing profile across the face of the wafer 11. One example of a fluid bearing is disclosed in U.S. Pat. No. 5,558,568. Another example is described in a patent application titled "Control Of Chemical-Mechanical Polishing Rate Across A Substrate Surface For A Linear Polisher;" Ser. No. 08/882,658; filed Jun. 25, 1997.

Figure 2:
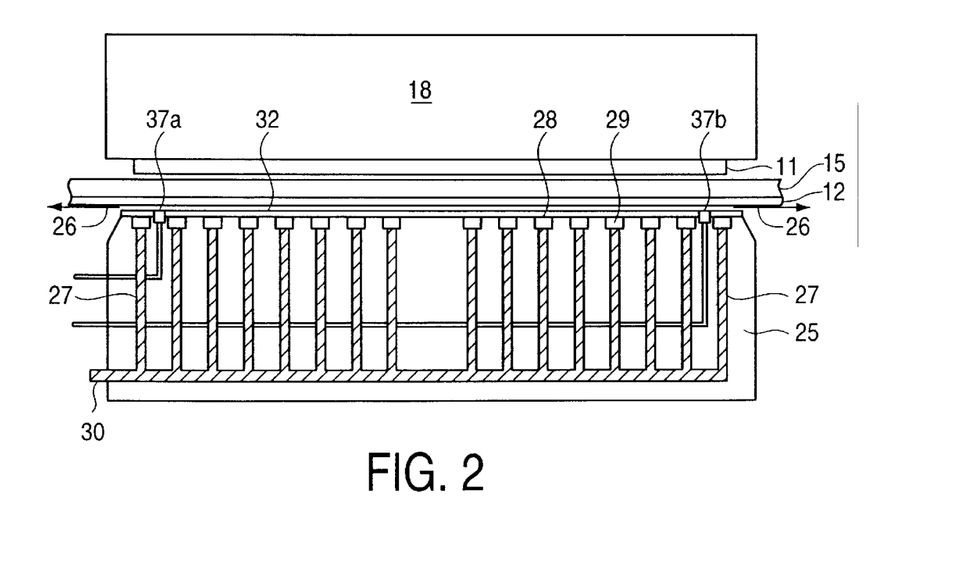
FIG. 2 is a cross-sectional view of a fluid bearing positioned under the belt/pad assembly and in which pressure sensors are disposed along the underside of the belt/pad assembly to measure pressure of the fluid residing between the underside of the belt/pad assembly and the fluid bearing.

As shown in FIG. 2, the fluid bearing 25 is positioned directly under the wafer 11, but on the opposite side of the belt 12. The wafer carrier 18 exerts a downforce to engage the wafer 11 on the pad 15, while the fluid flow from the fluid bearing exerts a counter-acting force to the underside of the belt 12. A plurality of channels 27 are distributed within the body of the bearing 25 with openings 28 disposed along the upper surface. In some instances, the channels 27 open into corresponding concentric grooves 29 formed along the upper surface region of the fluid bearing 25, so that fluid flow from a given opening 28 feeds fluid into the corresponding groove or grooves 29.

Figure 3:
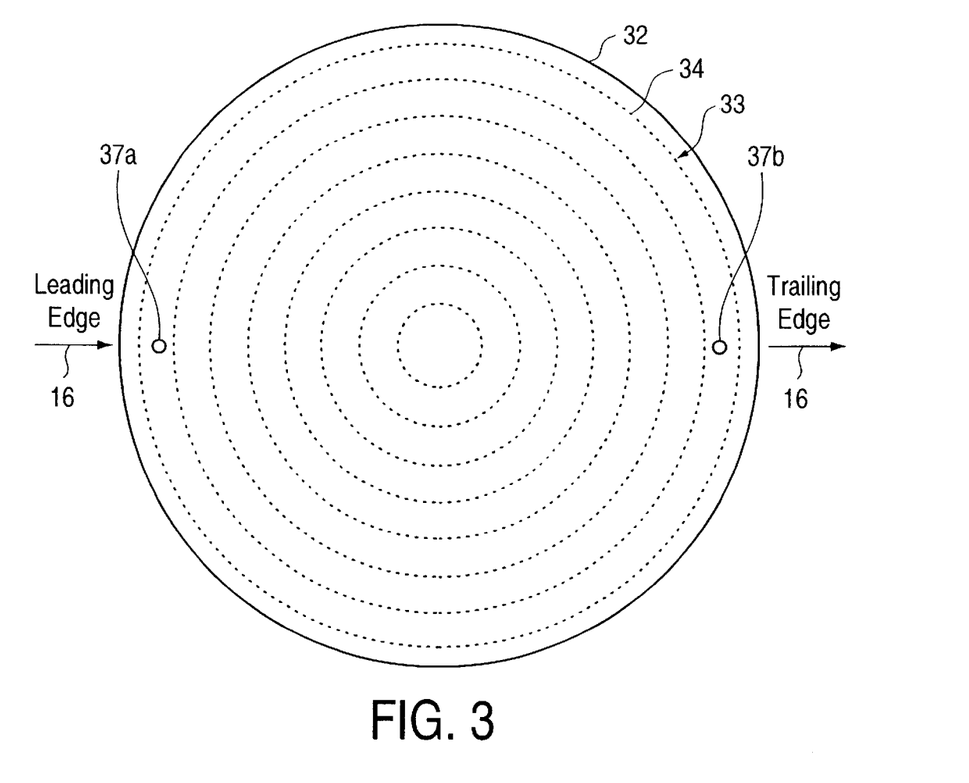
FIG. 3 is a top view of a cover plate having concentric arrangement of fluid openings for placement on the top surface of the fluid bearing of FIG. 2.

A cover plate (or insert) 32, also shown in FIG. 3, is then placed atop the bearing 25 to fit over the grooves 29. A plurality of openings 34, arranged in concentric rings 33, are distributed on the cover plate 32, so that each ring 33 coincides with a corresponding groove 29. Thus, in the example, the openings 34 of each concentrically arranged ring 33 are fed by fluid flow from the corresponding groove 29. A single inlet 30 is shown for feeding each of the channels 27. However, it is appreciated that the channels 27 could be coupled separately or in groups to separate inlets for individual (or group) flow control. FIGS. 2 and 3 show just one arrangement of openings on the surface of the bearing 25 to discharge the fluid and that the concentrically arranged openings 34 are but one example of how the openings can be configured.

In addition, by regulating or adjusting the fluid flow to the channels 27, the fluid pressure at the openings 28 can be regulated or adjusted, as well. That is, by adjusting the fluid flow at the inlet 30, fluid pressure at the openings 34 can be adjusted. The above-mentioned patent application titled "Control Of Chemical-Mechanical Polishing Rate Across A Substrate Surface For A Linear Polisher" describes a fluid bearing having adjustable fluid pressure at the openings. Furthermore, it is appreciated that each channel, a grouping of channels or portions of one or more rings can be configured for independent fluid pressure control. Thus, fluid pressure at different locations along the bearing surface can be controlled or adjusted separately. Again, although only one example is shown, a variety of fluid bearings can be implemented for the fluid bearing 25. The number of such fluid channels, openings and arrangement are design choices.

As noted previously, it is desirable to monitor the on-going process and determine at what point the polishing should be stopped. In order to provide for an end-point detection of an on-going process, the present invention uses sensors 37 to determine the end-point of a polishing process. In the example shown in FIGS. 2 and 3, the sensors are disposed within the fluid bearing 25. It is appreciated that a number of sensors 37 can be located at various sensing points along the surface of the fluid bearing or they can be located elsewhere (even away from the bearing itself), in which instance such sensors are coupled to sensing input locations along the surface of the fluid bearing by the use of electrical, hydraulic or pneumatic lines, etc.

In FIGS. 2 and 3, two sensors 37 (noted as sensors 37a and 37b) are shown disposed along the surface of the fluid bearing 25. The exact number and placement of such sensors is a design choice, but may be dependent on the type of parameters being measured or information being sought. The sensors employed can measure a variety of parameters which can provide information relating to the on-going polishing process. U.S. Pat. No. 5,762,536 describes the use of sensors for monitoring various polishing parameters. The example illustrated in the '536 patent shows five sensors dispersed along the face of the platen. One type of sensor employed is a pressure sensor to measure the pressure exerted by the fluid flowing between the fluid bearing 25 and the underside of the belt 12.

In the example, two sensors 37a–b are shown. A leading edge sensor is labeled 37a and a trailing edge sensor is labeled 37b. The leading edge is defined as the edge of the wafer 11 first making contact with a point located on the linearly moving pad 15. Alternatively, the trailing edge is defined as the edge of the wafer 11 where the pad 15 disengages from the wafer. Thus, the leading edge sensor 37a is disposed near the edge where a point on the belt 12 first engages the fluid bearing 25, while the trailing edge sensor 37b is located at the opposite edge of the bearing 25 along the linear direction traveled by the belt 12.

In the practice of the present invention, pressure sensors are utilized for sensors 37a–b. During a polishing operation, the fluid flow onto the fluid bearing 25 disperses fluid along the surface of the fluid bearing 25. Since the belt 12 is within close proximity of the bearing surface, the area between the fluid bearing 25 and the underside of the belt 12 is also filled with the fluid. Adequate fluid flow ensures that this space is filled with fluid, so that pressure sensors 37 will measure the pressure of the dispersed fluid. Again, U.S. Pat. No. 5,762,536 describes the use of pressure sensors to measure fluid pressure.

It is also understood that the variations in the force exerted at a particular location during polishing will cause an increase (or decrease) in the pressure being exerted onto the fluid at that location. That is, if base parameters, such as downforce of the wafer, fluid pressure of the fluid from the fluid bearing and pad velocity remain constant, the fluid pressure will typically remain somewhat constant as well. However, if certain polishing parameters are changed, then forces acting on the wafer-pad interface can cause a pressure difference that will be sensed by the pressure sensors. The present invention utilizes this change in the fluid pressure to detect when a particular end point is reached.

Figure 4:
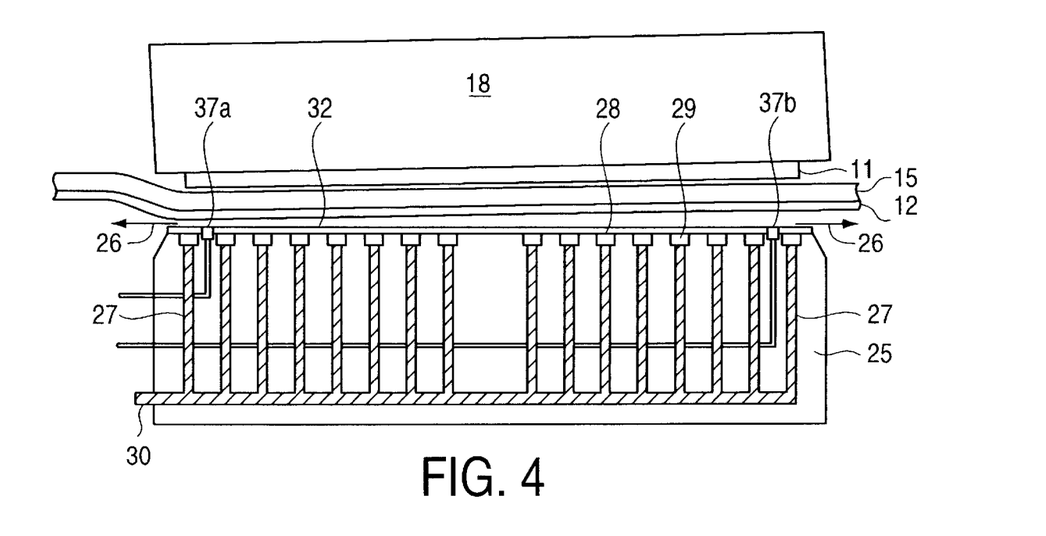
FIG. 4 is a cross-sectional view of a wafer residing above the pad and in which a change in the polishing response is noted by a leading edge sensor, when the pressure of the fluid changes at the leading edge of the wafer.

FIG. 4 illustrates one instance where there is a change in the fluid pressure.

In the example of FIG. 4, the wafer 11 is shown tilted slightly so as to depress the leading edge of the pad downward towards the sensor. Assuming the other parameters had been kept constant, this slight tilt causes the fluid pressure under the leading edge region to increase. The pressure increase is noted by the leading edge sensor 37a. That is, changes in the pressure at the leading edge can be detected by the leading edge sensor 37a. In some instances, the motion of the wafer 11 may cause an increase of fluid pressure at the leading edge and a slight decrease at the trailing edge, or vice versa. Accordingly, depending on the process, some process variations can be detected by a change in the pressure at the leading edge, the trailing edge, or the pressure differential between the leading edge and trailing edge locations.

This monitoring of the increase (or decrease) in the fluid pressure can be utilized to identify certain process parameters. The present invention looks at the fluid pressure changes to detect an end point condition. It has been determined through experimentation that the pad/wafer sliding interface results in a shear force that is counteracted by a gradient in the fluid bearing pressure within the bearingbelt gap. This resulting pressure gradient is generally in the direction of belt travel, so that an increase in the shear force will increase the pressure at the leading edge region, somewhat similar to the result obtained in the illustrated example of FIG. 4.

It has also been determined through experimentation that the shear force will depend on the material being polished. Accordingly, a change in the material being polished will change the magnitude of the shear force, which causes a change in the pressure at the leading edge of the fluid bearing. This pressure change, when appropriately monitored, can identify an end point condition. That is, when one material is polished away to reveal an underlying material of different composition (the end point of the polishing process), the shear force changes accordingly. The change in the shear force causes a change in the fluid pressure, most notably at the leading edge. This fluid pressure change is detected by the leading edge pressure sensor 37a. Therefore, a polishing end point can be detected by noticing a change in the fluid pressure residing above the fluid bearing 25.

Figure 5:
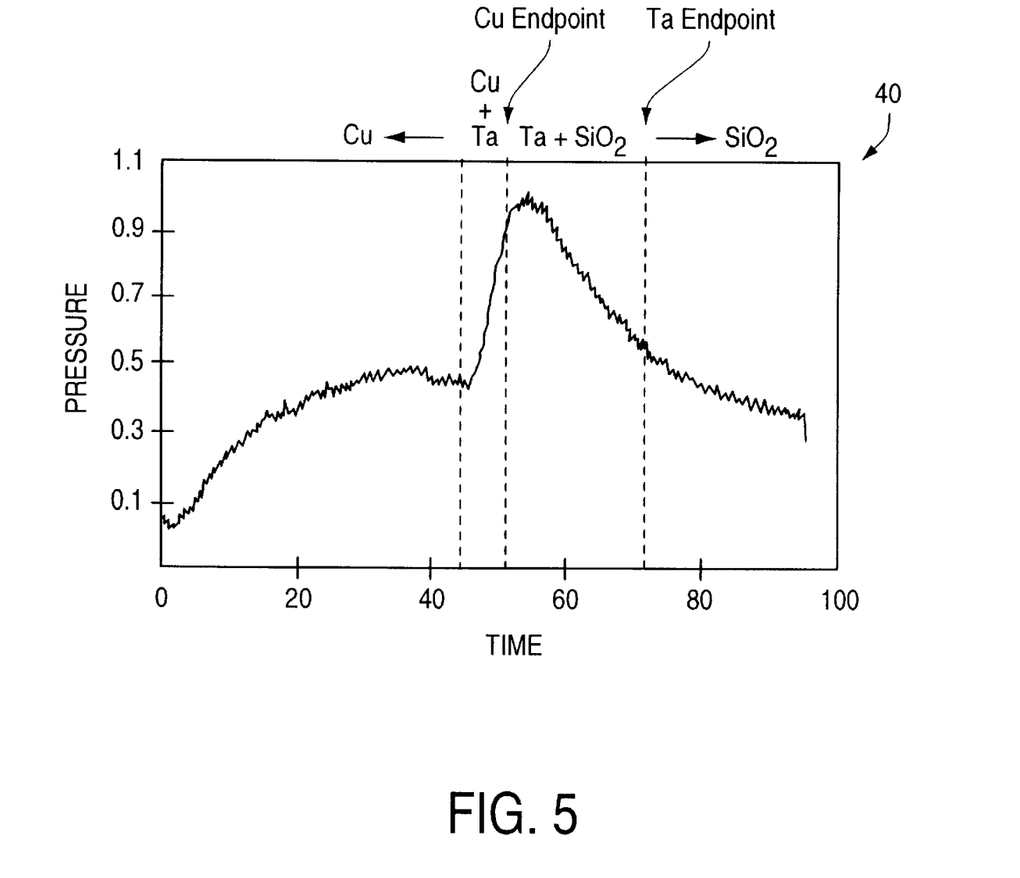
FIG. 5 is a graph showing a pressure profile measured by the leading edge sensor when different materials are polished.

Referring to a graph 40 of FIG. 5, one exemplary pressure curve for detecting a polishing process end point is illustrated. In the example experiment, a material stack comprised of copper/tantalum/silicon dioxide on a silicon wafer ($Cu/Ta/SiO_2/Si$) was polished using CMP on a linear planarization tool. Normalized fluid pressure values at the leading edge sensor 37a is graphed versus polishing time (arbitrary time scale is noted in the Figure). The $Cu/Ta/SiO_2/Si$ stack is equivalent to the polishing of copper (which is separated from the $SiO_2$ by a thin barrier layer of tantalum).

As noted in the graph 40, the fluid pressure increases slightly as the Cu is polished away. Then, as the underlying Ta begins to be exposed so that both Cu and Ta are being polished, a rapid increase in the fluid pressure is noted. A peak pressure is reached where only Ta is being polished. Subsequently, as Ta is polished away exposing the underlying $SiO_2$, the fluid pressure begins to decline and continues to do so until all of the Ta is removed.

It is apparent from the graph 40 that a desired polishing end point can be detected by monitoring the fluid pressure. In this instance, at the leading edge of the fluid bearing 25 by sensor 37a. The first abrupt change noted in the graph 40 occurs when Ta begins to be polished, culminating near a peak value when Cu has been polished away. Thus, Cu polishing end point can be determined at or near the peak fluid pressure value (as noted in the drawing). Similarly, if Ta removal is also desired, Ta polishing end point can be detected when the fluid pressure drops from the peak and reaches a preset value (also noted in the drawing). At this point, Cu and Ta will have been removed from above the ILD, so that the exposed Cu would reside in the openings formed in the ILD.

Figure 6A:
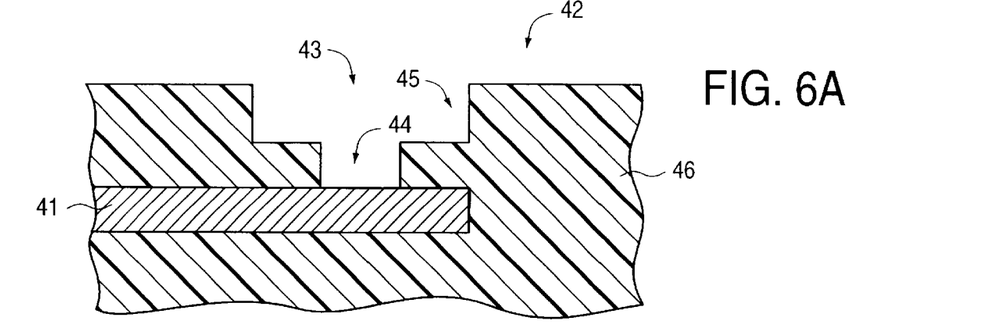
FIG. 6A is a cross-sectional view of a portion of a semiconductor device having a dual damascene structure formed in a dielectric layer and in which a via opening provides a connection to an underlying metal layer.
Figure 6B:
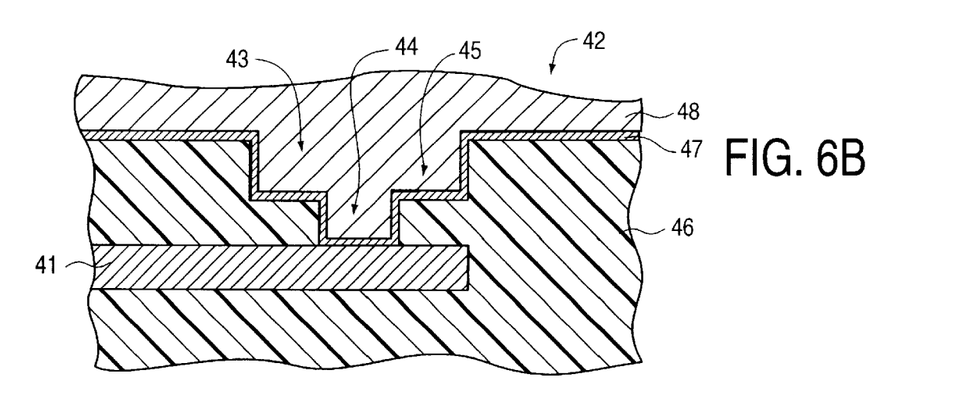
FIG. 6B is the device of FIG. 6A in which a barrier layer and a subsequent copper layer is deposited to fill trench and via openings of the dual damascene structure.
Figure 6C:
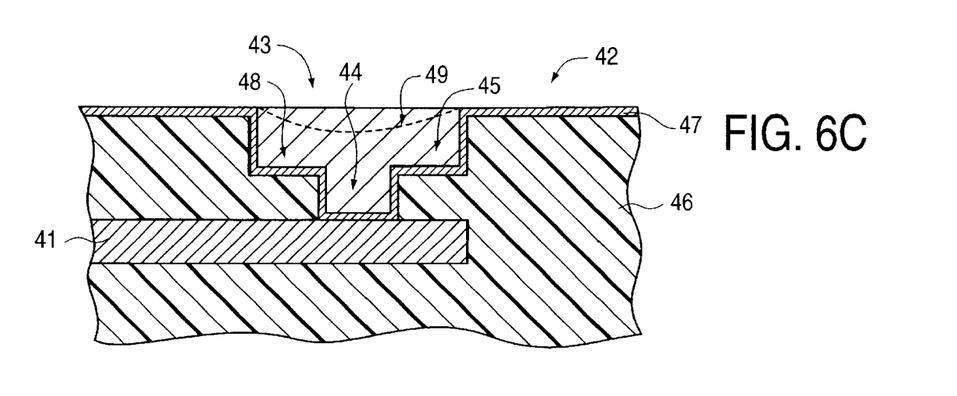
FIG. 6C is the device of FIG. 6B in which chemical mechanical polishing is employed to planarize the surface to remove excess copper and barrier material not within the trench and the via.

Referring to FIGS. 6A–C, an example application for practicing the present invention on a dual damascene structure is illustrated. In FIG. 6A, a portion of a semiconductor device 42 having a dual damascene structure 43 is shown. The dual damascene structure 43 is comprised of a via opening 44 and a contact trench opening 45 and is formed in a dielectric layer 46, which is typically referred to as an ILD. The via 44 is utilized to connect to an underlying conductive region. In the example, via 44 connects to an underlying metal layer 41.

Subsequently, a barrier layer 47 is deposited. One of the barrier materials previously described (such as TiN, Ta, TaN) is deposited as a barrier liner when copper metallization is utilized, since copper will readily diffuse into the ILD. Typically, the barrier layer is conformally deposited. Next, copper 48 is deposited over the wafer to fill in the via and trench openings 44, 45. When aluminum metallization is used, a barrier layer to isolate the metal from the ILD is typically not necessary.

Then, as shown in FIG. 6C, CMP is utilized to planarize the surface of the structure, so that the copper 48 remaining is only within the via and trench regions. Thus, the dual damascene structure is copper-filled. The CMP planarization is achieved by the practice of the linear planarization technique and the end point for the CMP is achieved by the practice of the present invention as previously described. When the copper and the barrier material are polished away, thereby exposing the underlying upper surface of the ILD, the fluid pressure changes being monitored will indicate when this end point has been reached. The CMP process is stopped. The dotted line 49 indicates what could result if the end point is not detected and the polishing is permitted to continue. The additional polishing can polish away portions of the metal residing within the trench region 45.

It is appreciated that equivalent material response graphs (like graph 40 of FIG. 5) can be experimentally obtained for the various materials being polished to detect the polishing end point. The response will also depend on the underlying material being exposed. Once experimentally obtained, the response curve can be utilized in a manufacturing setting to monitor an on-going process to detect an end point of a CMP polishing step. Accordingly, in-situ end point detection can be practiced in which the end point detection sensor is located below the polishing pad.

In the example described, two pressure sensors 37a, 37b are utilized. However, the pressure being monitored is from the leading edge sensor 37a. Thus, the present invention can be practiced utilizing only one sensor 37, which is located at the leading edge for optimum response. It is appreciated that the sensor 37a could be located elsewhere as well to provide the end point detection. However, the preference is to have it at the leading edge. The second sensor 37b is utilized for providing a fluid pressure response at the trailing edge, but is not necessarily needed for the practice of the present invention. The second sensor 37b is utilized in the for providing a fluid pressure response at the trailing edge for comparison purpose with the leading edge sensor. For example, pressure differential between the two sensor locations can be monitored for polishing uniformity of a given layer. The pressure differential of the two sensors could also be used for end point detection, instead of just the leading edge sensor. The use of particular sensor or sensors and the location of such sensor(s) will depend on the polishing process being monitored.

Accordingly, the present scheme monitors the fluid pressure between the fluid bearing and the underside of the belt to obtain end point detection of a CMP process. It is appreciated that the sensors described are pressure sensors, but other types of sensors can be readily adapted for measuring the change in the shear force or effects caused by such changes. It is also understood that the fluid bearing can be operated either with air gas or liquid, but the preference is to use air or de-ionized (D.I.) water.

The above example illustrates a condition where the change in the shear force is appreciable, so that a noticeable pressure change is detected at the process end point. Generally, a transition between dissimilar metals having different hardness or between a metal and a dielectric will result in a noticeable change in the shear force, which then can be detected by the pressure sensor. However, when materials having similar properties are being polished, the transition from one to the other may not result in an appreciable change in the shear force. For example, polishing of one dielectric to expose another may be difficult to detect due to the closeness of the forces associated with the materials involved.

For example, when an oxide and a nitride are the two materials involved, the end point detection is difficult to achieve, since the two materials have very similar properties. In those situations where it is difficult to detect the polishing end point, some other factor will need to be considered. The present invention looks to the zeta potential of the materials involved and selects a particular slurry which can enhance the detection of the polishing end point, by introducing a zeta potential of an opposite polarity. That is, the present invention utilizes or exploits the difference in the zeta potential between materials to determine the polishing end point. The zeta potential difference enhances the frictional shear force differential, so that the above described fluid pressure sensing technique can still be used to provide the end point detection.

It is known that abrasive particles in colloidal suspension in the slurry acquire an electric charge and remain in suspension because of mutual electrostatic repulsive force. There exists a charge distribution between the charged colloidal particle and the bulk of the solution in the slurry. The presence of this charge results in a potential difference between the surface of the abrasive particle and the solution. The potential at the surface of the abrasive particle (also referred to as colloid) is referred to as the surface potential.

Another potential, referred to as zeta potential, occurs at the junction or boundary of the moving particle and the liquid. This boundary (also referred to as the slip plane) is defined as the point where the Stern layer and the diffuse layer meet. The Stern layer is considered to be rigidly attached to the colloid, while the diffuse layer is not (see "Zeta Potential: A complete course in 5 Minutes;" Zeta-Meter Inc. brochure at pp. 1–8). The electrical potential at this junction is related to the mobility of the particle, and believed to be more significant than the surface potential. The zeta potential of the particle can be easily measured under the influence of an electric field. For example, a Coulter Delsa 440 SX Zeta Potential and Particle Size measuring tool (by Coulter International Corp.) measures the electrophoretic mobility by laser Doppler velocimetry to determine the zeta potential.

The zeta potential is also related to the repulsion and attraction forces of two particles. Generally, stability of particles in suspension is determined by a balance of two opposing forces. One is the electrostatic repulsive force, while the other is the van der Waals attractive force (see, the Zeta-meter Inc. reference noted above). Particles overcoming the electrostatic repulsion barrier typically will agglomerate. Thus, monitoring the zeta potential can identify the behavior of the particles in the solution. Similarly, by manipulating the zeta potential, the behavior of the particle in the solution can also be controlled. For example, fluid viscosity, flocculation and coagulation are some properties which can be controlled by adjusting the zeta potential of a fluid.

Figure 7:
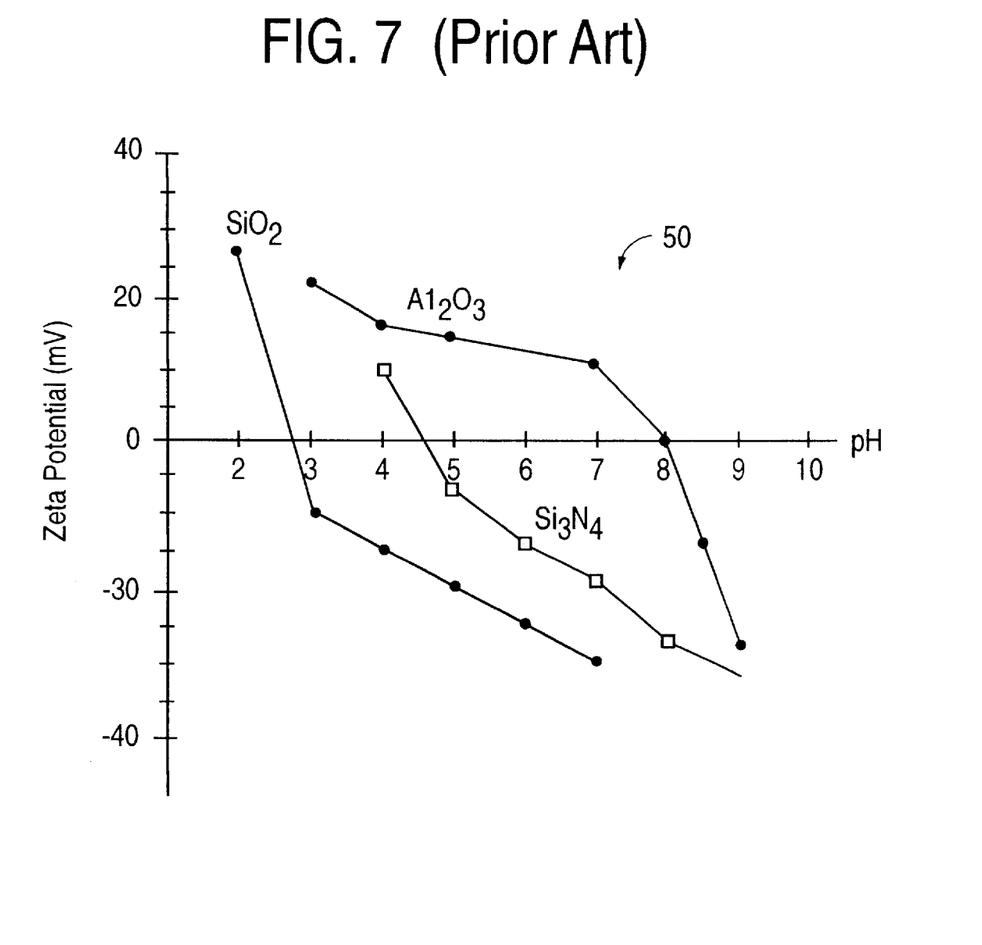
FIG. 7 is a graphic representation showing zeta potential versus pH for three different materials.

Referring to FIG. 7, graph 50 illustrates the zeta potentials of three compounds as the pH level changes. The graph 50 shows the zeta potential versus pH for $SiO_2$, $Si_3N_4$ and $Al_2O_3$. As noted in the graph 50, the zeta potential for each of the compounds is dependent on the pH level of the medium. In each case, the zeta potential changes polarity at a given pH level. Accordingly, the pH level of the medium can be selected so that the zeta potential of the particles present in the slurry will be at a particular value and polarity.

The present invention exploits this zeta potential variation to detect an end point of a CMP processing step. From the above description, it is appreciated that the abrasive particles present in the slurry possess a zeta potential, which affects how the particles respond to the polishing (or planarizing) process. Likewise, the film surface (of the material being polished) immersed in the slurry also acquires surface and zeta potentials as the material is polished. The zeta potential of the film will be separate from the zeta potential of the abrasive particles. With proper selection of a pH operating level, the abrasive particles of the slurry can be selected to have a zeta potential of one polarity, while the film material being polished can be selected to have a zeta potential of the opposite polarity.

An example of this practice is illustrated below. From the graph 50, it can be inferred that the zero zeta potential (or zeta potential polarity cross-over) point is approximately at a pH of 2.7 for $SiO_2$ and 4.5 for $Si_3N_4$. Thus, it can be interpreted that a slurry having a pH level in the range of 3 to 4, will cause the $SiO_2$ material to have a negative zeta potential, while $Si_3N_4$ material will have a positive zeta potential. If the slurry selected has $SiO_2$ abrasive particles suspended in the solution, at a pH of 3 to 4, the $SiO_2$ particles will have a negative zeta potential value. If this slurry is initially used to polish a $SiO_2$ film layer, both the $SiO_2$ slurry particles and the $SiO_2$ film will have a negative zeta potential. There is no appreciable difference in the zeta potentials of the abrasive particles and the film layer being polished.

However, if the film being polished is a $Si_3N_4$ film layer, the zeta potential of $Si_3N_4$ would be positive at the pH range of 3 to 4. The zeta potential polarity of the $Si_3N_4$ film is opposite from that of the $SiO_2$ abrasive particles of the slurry. The polarity difference in the zeta potentials of the abrasive particles and the film layer being polished is exploited to detect the end point of a polishing process.

Assuming that the layer being polished away is $SiO_2$ and the underlying layer is $Si_3N_4$. Since the $SiO_2$ is being polished away to expose the underlying $Si_3N_4$, it would be beneficial to stop the polishing process when the $Si_3N_4$ is exposed. While the $SiO_2$ is being polished, the zeta potential will have a negative value for the material being polished. When the $Si_3N_4$ is exposed, the $Si_3N_4$ film will exhibit a zeta potential of the opposite polarity. This noticeable change in the zeta potential is exploited to provide a detection mechanism for determining the endpoint for polishing away the $SiO_2$ layer.

The above example illustrates the practice of the invention in which the zeta potential can be exploited to determine the end point of a CMP process. The zeta potentials can be selected so that when one layer (or portion of a layer) is polished away to expose an underlying layer, a noticeable change occurs in the zeta potentials of the materials involved. A monitoring scheme can then detect this change in the zeta potentials.

A variety of techniques can be used to ensure that the two materials will have differing zeta potentials when being polished. Specialized slurry chemistries can be selected, additives can be introduced into the slurry, or other means which ensure a differing zeta potential between the two materials being polished can be employed. The preferred technique controls the pH operating level of the slurry to ensure a point of operation which causes the two materials (the material being polished and the underlying material) to have noticeable zeta potential differences. The preferred technique is to ensure that the two materials have opposite zeta potential polarities at the operating pH of the slurry. Thus, when the overlying layer is polished away to expose the underlying layer (at which point the polishing should terminate), a polarity change in the zeta potential occurs. This polarity difference is exploited to detect the end point for the polishing.

Referring again to the $SiO_2/Si_3N_4$ example described above where the polishing of the $SiO_2$ film is achieved by the abrasive $SiO_2$ particles of the slurry, both will have negative zeta potentials at a slurry pH level in the range of 3 to 4. As long as the $SiO_2$ is being polished, the particles in the slurry and the film will be in electrostatic repulsion, due to the negative zeta potentials. Then, when the $Si_3N_4$ is exposed, the positive zeta potential of the $Si_3N_4$ film will introduce an attractive force to the abrasive particles of the slurry. This attraction force will then induce an increase in the frictional force, since the particles tend to combine (amalgamate). This increase in the frictional force is manifested as an increase in the shear force at the wafer-pad interface and detected as an increase in the fluid pressure at the leading edge sensor 37a.

Figure 8A:
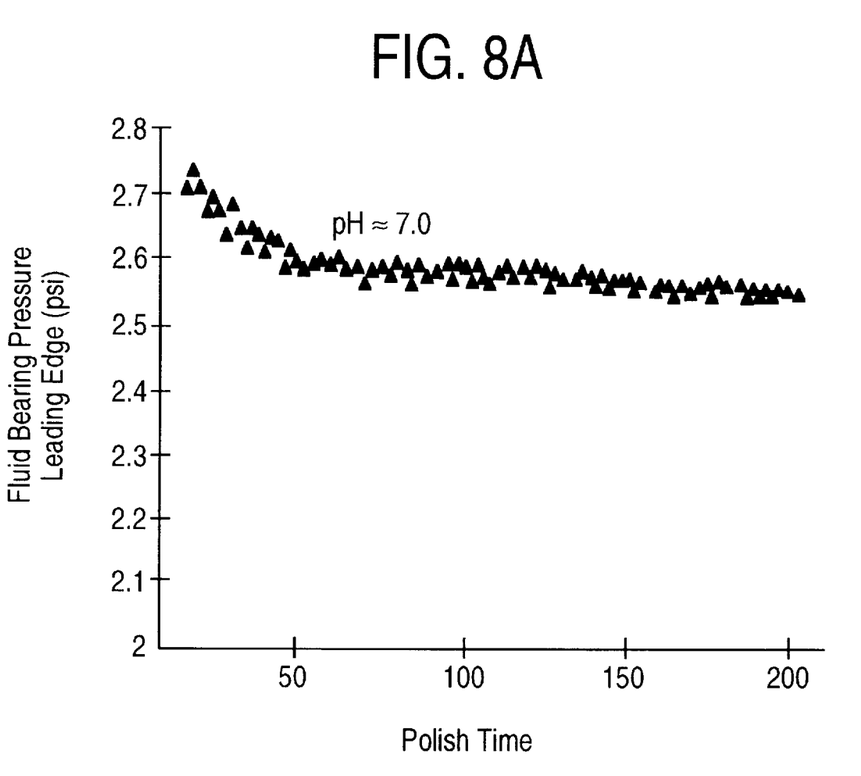
FIG. 8A is a graph showing a pressure profile measured by the leading edge sensor when a PTEOS/$Si_3N_4$/$SiO_2$ stack is polished with a slurry having a pH of approximately 7.0.

Experimental results of detecting a CMP end point in polishing a film stack of $PTEOS/Si_3N_4/SiO_2$ disposed on a Si wafer are shown in FIGS. 8A and 8B, in which the leading edge sensor of a fluid bearing is used to detect the fluid pressure change. PTEOS (plasma enhanced tetra ethyl ortho silicate glass) is a form of silicon dielectric having properties similar to $SiO_2$. A silica-based slurry having a pH level of approximately 7.0 is selected for performing the CMP. As illustrated, no appreciable change occurred in the pressure of the fluid at the leading edge sensor, since the zeta potentials are not noticeably different for the PTEOS ($SiO_2$) and $Si_3N_4$ at this pH level (see graph 50 of FIG. 7) of approximately 7.0.

Figure 8B:
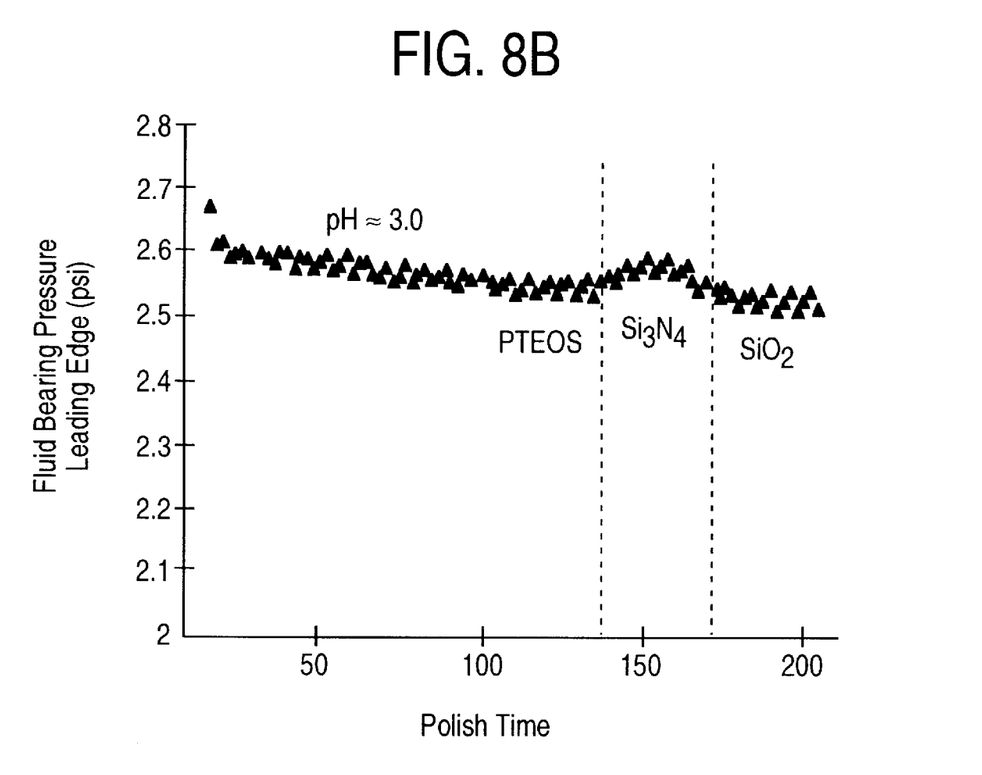
FIG. 8B is a graph showing a pressure profile measured by the leading edge sensor when the PTEOS/$Si_3N_4$/$SiO_2$ stack of FIG. 8A is polished with a slurry having a pH of approximately 3.0.

However, in FIG. 8B, a noticeable change in the fluid pressure occurred when the $PTEOS/Si_3N_4$ structure was exposed to a different slurry during polishing. In this instance, a silica-based slurry having a pH level of approximately 3.0 is selected for performing CMP. As described above, the zeta potential polarity shift occurs when the PTEOS is polished away and the $Si_3N_4$ is exposed at this pH level. An appreciable increase in the leading edge fluid pressure is noted when $Si_3N_4$ is exposed and commences to be polished. This difference is attributed to the difference in the zeta potentials between PTEOS and $Si_3N_4$. In this instance, a polarity reversal occurs from one material to the next, which is manifested in the increased fluid pressure. Subsequently, as the $Si_3N_4$ is polished away exposing the underlying $SiO_2$ material, the fluid pressure then returns near the earlier level.

It is to be reiterated that the experimental parameters between the two FIGS. 8A–B were the same, except that in FIG. 8B, the pH of the slurry was selected near 3.0, instead of near 7.0. As noted in FIG. 7, at a pH level near 3.0, the zeta potentials are of different polarity for $SiO_2$ and $Si_3N_4$.

Thus, as PTEOS ($SiO_2$) is polished away to expose the underlying $Si_3N_4$, the appreciable zeta potential change causes a change at the wafer-pad interface. In the particular example, a change in the zeta potential polarity causes the $Si_3N_4$ film to be attracted to the abrasive particles of the slurry, which induces an increase in the shear force at the wafer-pad interface. This increase in the shear force is detected at or near the leading edge by the sensor 37a, as an increase in the fluid pressure residing between the belt and the fluid bearing.

It is appreciated that the sensor 37a could be located elsewhere as well to provide the end point detection. However, the preference is to have it at the leading edge. The second sensor 37b is utilized in the present instance for providing a fluid pressure response at the trailing edge for comparison purpose with the leading edge sensor. For example, pressure differential between the two sensor locations can be monitored for polishing uniformity of a given layer. The pressure differential of the two sensors could also be used for end point detection, instead of just the leading edge sensor.

As noted above, when detecting a polishing end point between materials having similar frictional properties, such as between oxides and nitrides, the technique of utilizing leading edge pressure variations is sometimes difficult or impossible to achieve without some form of additional aid. In the practice of the present invention, the zeta potential is exploited to differentiate a response characteristic when one material is polished away exposing an underlying material. Although the zeta potential can be monitored for its value, the present invention detects the effects of the zeta potential variation by measuring the fluid pressure disposed between the fluid bearing and the belt/pad assembly. A particular slurry pH level is selected to cause the zeta potential of the two materials to have opposite polarity at that pH level, so that the difference in the polarity causes a noticeable change in the frictional force, which is detected by the fluid bearing pressure sensor. In this particular instance, the sensor utilized is the leading edge sensor of the linear polisher.

An application of the above described CMP process to planarize a $SiO_2$ layer, in which $Si_3N_4$ is used for the polishing end point is illustrated in FIGS. 9A–F. Referring to FIGS. 9A–F, a structure 60 is shown, having a silicon substrate 61 upon which a $SiO_2$ layer 62 is formed. Atop the $SiO_2$ layer 62, a $Si_3N_4$ layer 63 is formed (see FIG. 9A). A photoresistive layer 64 is deposited and patterned to expose portions of the substrate 61 (see FIG. 9B). Then, using a known etching step, the exposed substrate is etched to form openings 65 (see FIG. 9C).

Figure 9A:
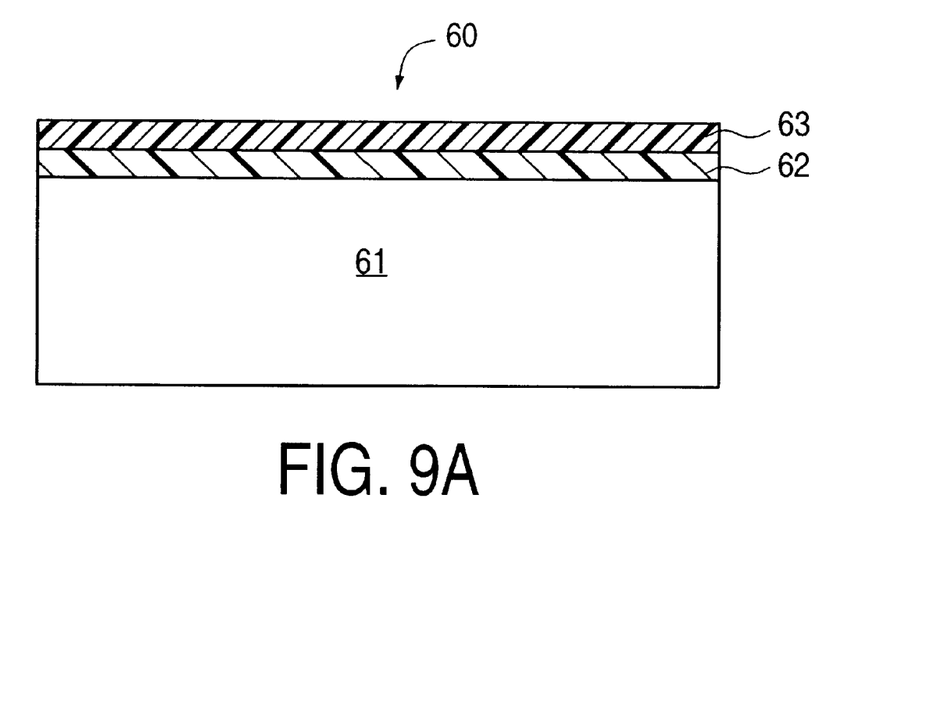
FIG. 9A is a cross-sectional view of a structure in which $SiO_2$ and $Si_3N_4$ layers are formed above a silicon substrate.
Figure 9B:
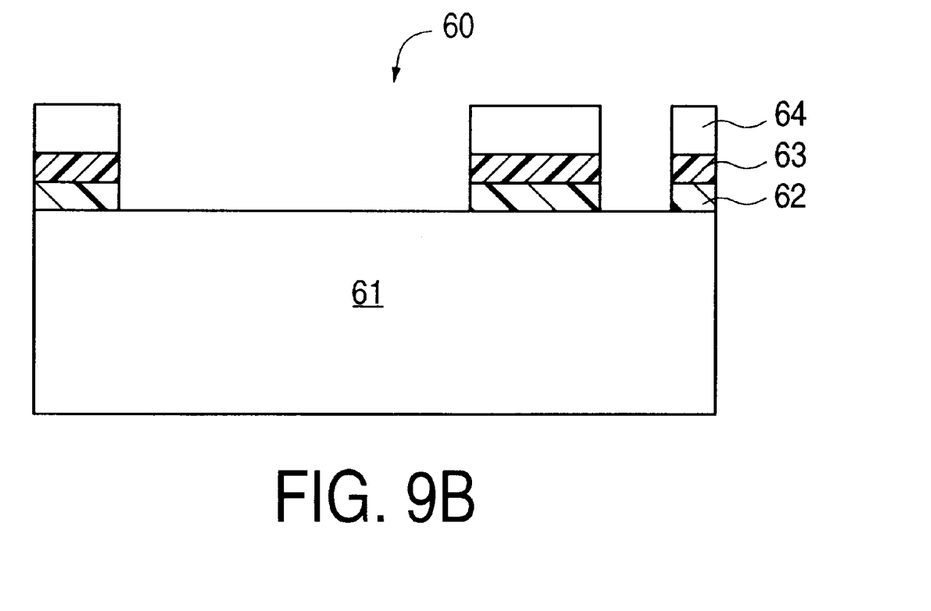
FIG. 9B is the structure of FIG. 9A in which a photoresistive layer is deposited and patterned to expose portions of the substrate.
Figure 9C:
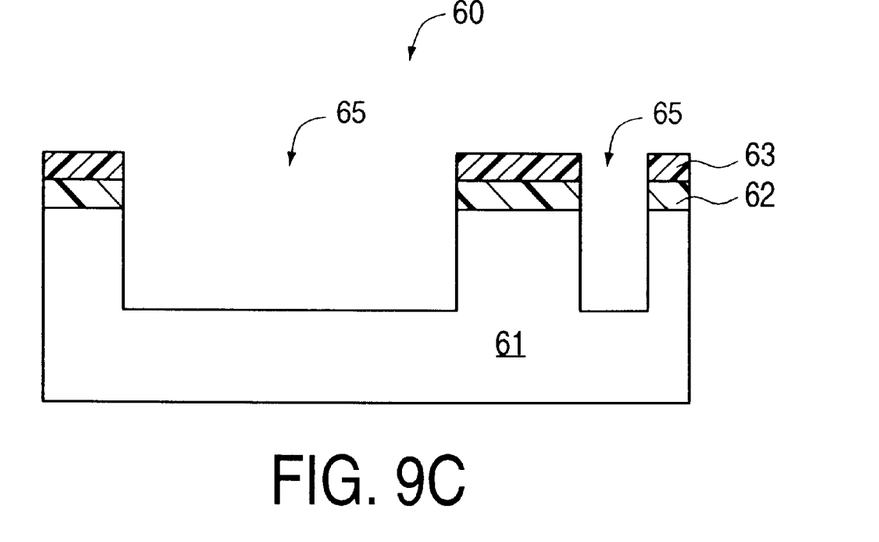
FIG. 9C is the structure of FIG. 9B in which the exposed portions of the substrate are etched to form openings.
Figure 9D:
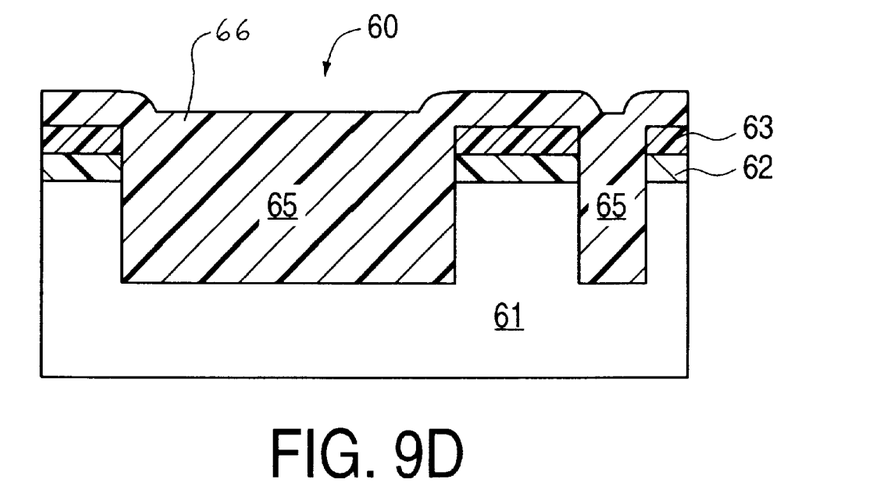
FIG. 9D is the structure of FIG. 9C in which a second $SiO_2$ layer is blanket deposited to cover the surface of the structure, also filling in the openings formed in the substrate.
Figure 9E:
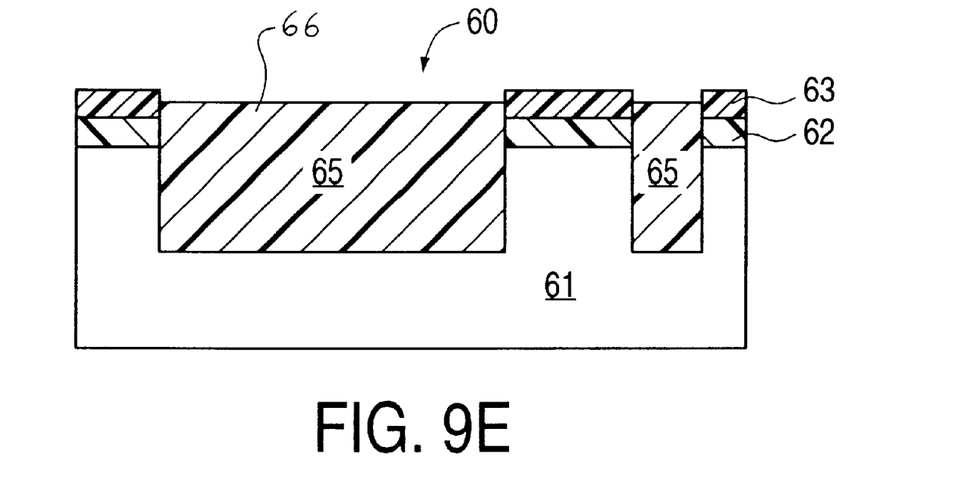
FIG. 9E is the structure of FIG. 9D in which CMP is employed to planarize the $SiO_2$ layer so that $SiO_2$ only remains in the openings formed in the substrate, the end point for the CMP process being determined by the exposing of the $Si_3N_4$ layer.
Figure 9F:
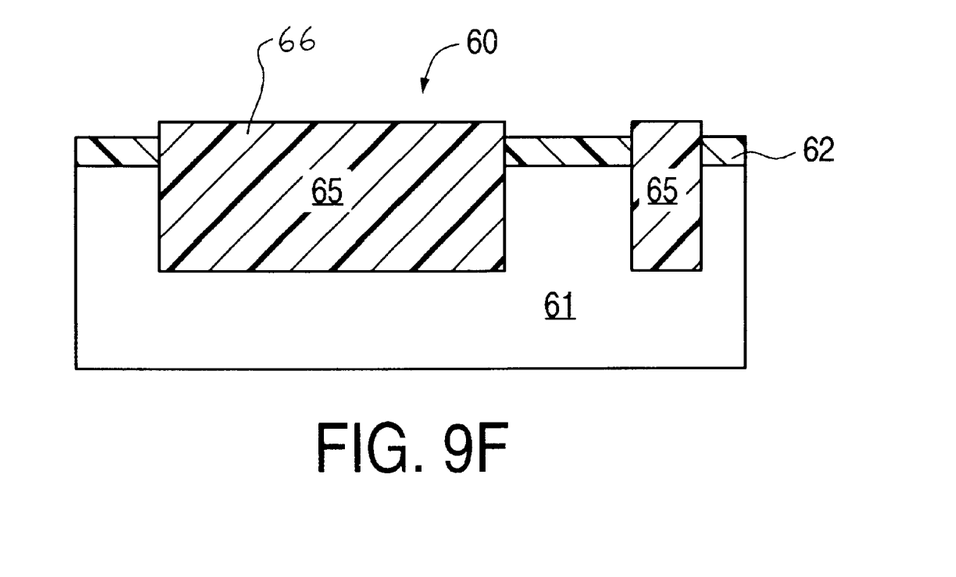
FIG. 9F is the structure of FIG. 9E in which the exposed $Si_3N_4$ layer is etched.

Subsequently, a second $SiO_2$ layer 66 is blanket deposited over the structure, also filling in the openings 65 (see FIG. 9D). Then, CMP is performed to planarize the $SiO_2$ layer 66. The end point detection scheme described above is employed to determine when the underlying portions of the $Si_3N_4$ layer 63 is exposed. The resulting structure has the $SiO_2$ in the openings 65, but not over the upper surface of the $Si_3N_4$ (see FIG. 9E). Typically, the upper surface of the $SiO_2$ in the openings 65 is slightly below the level of the $Si_3N_4$ layer 63. Then, the exposed $Si_3N_4$ layer 63 is etched away by a known technique, so that the upper surface of the structure is covered by $SiO_2$ (see FIG. 9F). The portion of the $SiO_2$ material 66 residing at the openings 65 is slightly higher as compared to the $SiO_2$ material 62 which had been residing below the $Si_3N_4$ layer 63. The structure formed is part of a shallow trench isolation structure. As noted above, the structure is formed by the application of CMP and in which the present invention can be practiced to detect the end point of the CMP step.

Thus, a scheme for monitoring the fluid pressure to obtain end point detection is described. It is appreciated that the sensors of the present invention are described in reference to a pressure sensor, but other types of sensors can be readily adapted for measuring the change in the shear force or effects caused by such changes. It is also understood that the fluid bearing can be operated with air, gas or liquid. In practicing the invention, the preference is to use air or de-ionized (D.I.) water, since these two sources of fluid are less costly to use. The zeta potential is controlled by selecting a pH level of the slurry. However, it is appreciated that other means are available to select proper zeta potential operation points, without departing from the spirit and scope of the present invention.

Furthermore, although the present invention is described in reference to performing CMP on a semiconductor wafer, the invention can be readily adapted to polish other materials as well, such as glass, metal substrates or other semiconductor substrates, including substrates for use in manufacturing flat panel displays.

We claim:

1. In a tool utilized to polish a first material associated with a first zeta potential and in which the first material is placed upon a polishing pad for polishing the first material to expose an underlying second material associated with a second zeta potential, an apparatus for determining a polishing end point for polishing the first material comprising:

a fluid bearing disposed along an underside of the pad opposite the first material for dispensing fluid between the fluid bearing and the pad;

a sensor coupled to the fluid bearing to measure a pressure change of the fluid when the end point for polishing the first material is reached;

a slurry dispensed onto the polishing pad for polishing the first material, the slurry having a selected pH value so that a zeta potential of the slurry is different from the second zeta potential, wherein upon completion of the polishing of the first material, the difference between the zeta potential of the slurry and the second zeta potential provides a pressure change of the fluid measured by the sensor; and a controller coupled with the sensor and operative to terminate polishing in response to the sensor measuring the pressure change provided by the difference in zeta potentials.

2. The apparatus of claim 1 wherein the presence of the second zeta potential causes the change in the fluid pressure when the underlying second material is exposed.

3. The apparatus of claim 1 wherein the first and second zeta potentials are of opposite polarity.

4. In a linear polisher for performing chemical-mechanical polishing (CMP) on a first surface of a substrate or of a layer formed on the substrate, and in which the substrate is placed upon a linearly moving polishing pad for polishing the first surface, wherein the first surface is associated with a first zeta potential and overlies a second surface associated with a second zeta potential, an apparatus for determining a polishing end point for polishing the first surface comprising:

a fluid bearing disposed along an underside of a linearly moving belt having the pad disposed thereon, the fluid bearing for dispensing fluid along a gap between the fluid bearing and the underside of the belt;

a sensor coupled to the fluid bearing to measure a pressure change of the fluid when the end point for polishing the first surface is reached;

a slurry dispensed onto the polishing pad for polishing the first surface, the slurry having a selected pH value so that a zeta potential of the slurry is different from the second zeta potential, wherein upon completion of the polishing of the first surface, the difference between the zeta potential of the slurry and the second zeta potential provides a pressure change of the fluid measured by the sensor; and a controller coupled with the sensor and operative to terminate polishing in response to the sensor measuring the pressure change provided by the difference in zeta potentials.

5. The apparatus of claim 4 wherein the presence of the second zeta potential causes the change in the fluid pressure when the second material is exposed.

6. The apparatus of claim 5 wherein the first and second zeta potentials are of opposite polarity.

7. The apparatus of claim 4 wherein the fluid bearing dispenses a liquid.

8. The apparatus of claim 4 wherein the fluid bearing dispenses air or gas.

9. In a linear polisher for performing chemical-mechanical polishing (CMP) on a first material layer formed on a semiconductor wafer, and in which the first material layer is polished to expose an underlying second material layer, wherein the first and second material layers are respectively associated with a first and second zeta potential, an apparatus for determining a polishing end point for stopping the polishing when the second material layer is exposed comprising:

a fluid bearing disposed along an underside of a linearly moving belt having the pad disposed thereon, the fluid bearing for dispensing fluid along a gap between the fluid bearing and the underside of the belt;

a sensor coupled to the fluid bearing to measure a pressure change of the fluid when the end point for polishing the first material layer is reached;

a slurry dispensed onto the polishing pad for polishing the first material layer, the slurry having a selected pH value so that a zeta potential of the slurry is different from the second zeta potential, wherein upon completion of the polishing of the first material layer, the difference between the zeta potential of the slurry and the second zeta potential provides a pressure change of the fluid measured by the sensor when the second material layer is exposed to the slurry; and a controller coupled with the sensor and operative to terminate polishing in response to the sensor measuring the pressure change provided by the difference in zeta potentials.

10. The apparatus of claim 9 wherein the first and second zeta potentials are of opposite polarity.

11. The apparatus of claim 10 wherein the pressure change is a result of a change in a shear force exerted at an interface of the pad and the material layers being polished, the change in the shear force being induced by the change of zeta potential polarity as the second material layer is exposed.

12. The apparatus of claim 9 wherein the sensor is located at a leading edge of the fluid bearing where a point on the pad first makes contact with the fluid bearing.

13. The apparatus of claim 9 wherein the fluid bearing dispenses a liquid.

14. The apparatus of claim 9 wherein the fluid bearing dispenses air or gas.

15. A method of determining a polishing end point for polishing a first surface associated with a first zeta potential, the first surface overlying a second surface associated with a second zeta potential, the method comprising:

dispensing a slurry onto a polishing pad for polishing the first surface, the slurry having a selected pH value so that detection of a change from the first zeta potential to the second zeta potential indicates a completion of the polishing of the first surface;

polishing the first surface;

detecting a change from the first zeta potential to the second zeta potential, thereby detecting a completion of the polishing of the first surface; and terminating polishing in response to the detected change from the first zeta potential to the second zeta potential.

16. The method of claim 15 further comprising placing a fluid along an underside of the pad, opposite the surface being polished, and detecting the change in the zeta potential by detecting a pressure change of the fluid.

17. The method of claim 16 wherein a sensor is coupled to measure the pressure change, which is caused by a change in a shear stress when the pad engages the second surface.

18. The method of claim 16 wherein dispensing of the slurry includes selecting a pH level for the slurry, so that the first zeta potential is opposite in polarity to the second zeta potential.

19. In a linear polisher for performing chemical-mechanical polishing (CMP) on a first material layer formed on a semiconductor wafer, and in which the first material layer is polished to expose an underlying second material layer, wherein the first and second material layers are respectively associated with a first and second zeta potential, a method of determining a polishing end point for stopping the polishing when the second material layer is exposed comprising:

dispensing a slurry onto a polishing pad for polishing the first material layer, the slurry having a selected pH value so that a zeta potential of the slurry is different from the second zeta potential, wherein upon completion of the polishing of the first material layer, the difference between the zeta potential of the slurry and second zeta potential provides a pressure change of a fluid dispensed along an underside of the pad or a belt upon which the pad is mounted;

polishing the first material layer;

measuring the pressure change of the fluid when the second material layer begins to be polished; and terminating polishing in response to the measured pressure change provided by the difference between the zeta potential of the slurry and second zeta potential.

20. The method of claim 19 wherein measuring the pressure change of the fluid includes measuring a change in a polishing sheer force of the wafer engaging the pad.

21. The method of claim 20 wherein a sensor is coupled to measure the pressure change, which is caused by a change in the polishing shear force when the pad engages the second material layer.

22. The method of claim 20 wherein dispensing of the slurry includes selecting a pH level for the slurry, so that the zeta potential of the slurry is opposite in polarity to the second zeta potential associated with the second material layer.

23. For use with a chemical-mechanical polishing (CMP) tool comprising a polishing pad operative to polish a first material layer formed on a semiconductor wafer positioned adjacent the polishing pad to expose an underlying second material layer, the first and second material layers respectively associated with a first and second zeta potential, a method of determining a polishing end point, the method comprising:

dispensing a slurry onto the polishing pad, the slurry having a pH value selected so that a zeta potential of the slurry is opposite in polarity from the second zeta potential;

exposing the second material layer by polishing the first material layer with the polishing pad;

when the second material layer is polished, measuring a pressure change of a fluid dispensed along an underside of the polishing pad, the pressure change being in response to the polarity difference between the zeta potential of the slurry and second zeta potential; and terminating polishing in response to the measured pressure change.

* * * * *